US006277889B1

(12) United States Patent
Bowen

(10) Patent No.: US 6,277,889 B1
(45) Date of Patent: Aug. 21, 2001

(54) MOLLUSCICIDE FORMULATION

(76) Inventor: Ivor Bowen, 23 Maes Cadwgan, Creigiau, Cardiff (GB), CF4 8TQ ( * ) Notice: Subject to any disclaimer, the term of this patent is extended or adjusted under 35 U.S.C. 154(b) by 0 days.

(21) Appl. No.: 09/423,938

(22) PCT Filed: May 13, 1998

(86) PCT No.: PCT/GB98/01258

§ 371 Date: Nov. 12, 1999

§ 102(e) Date: Nov. 12, 1999

(87) PCT Pub. No.: WO98/51150

PCT Pub. Date: Nov. 19, 1998

(30) Foreign Application Priority Data

May 15, 1997 (GB) .................................................. 9709853

(51) Int. Cl.$^7$ .......................... A01N 37/44; A01N 35/06; A01N 35/00; A01N 35/02; A01N 43/02

(52) U.S. Cl. .......................... 514/693; 514/449; 514/450; 514/452; 514/535; 514/536; 514/537; 514/690; 514/698; 514/705; 514/918; 514/919; 514/920; 424/84; 424/78.37; 424/78.38; 424/DIG. 10

(58) Field of Search ..................................... 514/535, 537, 514/567, 690, 692, 693, 919, 918, 449, 450, 452, 536, 698, 705, 920; 424/78.37, DIG. 10, 84, 78.38; 43/131

(56) References Cited

U.S. PATENT DOCUMENTS

| 2,967,128 | * | 1/1961 | Kare ..................................... 514/535 |
| 4,765,979 | * | 8/1988 | Nielsen .................................. 424/84 |
| 4,940,583 | * | 7/1990 | Thompson ............................ 424/736 |

FOREIGN PATENT DOCUMENTS

314846 * 11/1987 (EP) .

OTHER PUBLICATIONS

Chemical Abstracts 122:207728, 1996.*

* cited by examiner

*Primary Examiner*—John Pak
(74) *Attorney, Agent, or Firm*—Factor & Partners, LLC

(57) ABSTRACT

A molluscicide containing a non-toxic animal repellant and metaldehyde, in which the molluscicidal efficacy of the molluscicide greater than that of the molluscicide if it did not contain repellant. The repellant may be an anthranilate compound or d-pulegone which present at a concentration of up to 1%.

17 Claims, 5 Drawing Sheets

MOLLUSCICIDE FORMULATION

This application is a 371 of PCT/GB98/01258, filed on May 13, 1998.

This invention relates to molluscicide formulations and in particular to molluscicide formulations for agricultural and horticultural purposes which act to repel non-targeted species while having an increased efficacy in killing a targeted species.

Prevention of damage to seeds and crops includes control of avian depredation and mammalian seed predators as well as consumption by mollusca. However, the ingestion of pesticides by non-targeted species can limit the use of such agricultural chemicals. To this end, a molluscicide formulation which concomitantly provides a non-toxic repellant to birds and mammals fulfils a need. Such a molluscicide formulation has advantages such as more specific targeting for a particular species, acting as a repellant to avert other species and being non-toxic to other species thereby reducing the hazard for non-targeted species.

According to a first aspect of the invention there is provided a molluscicide formulation containing a non-toxic animal repellant and metaldehyde. It has been found that combining a non-toxic animal repellant with metaldehyde in a molluscicide formulation has a synergistic effect on the efficacy of the molluscicide formulation; i.e. the molluscicide formulation kills a greater number of mollusca than i f the molluscicide formulation did not contain the repellant. The animal repellant may be a bird and/or mammal repellant.

Such a molluscicide formulation has a number of advantages. It is more efficient at killing a targeted pest and so reduces damage to crops and seeds. It also helps to avert avian and mammalian pests from crops and seeds and so reduces damage by the pests. Further, as the repellant is non-toxic to avian and mammalian species it does not provide a hazard to them and so may be employed as a pesticide in situations in which toxic repellents may not be used.

The repellant may be an anthranilate compound. Preferably the anthranilate compound is selected from methyl anthranilate, isobutyl anthranilate, ethyl anthranilate, isobutyl methyl anthranilate and dimethyl anthranilate. More preferably the repellant is methyl anthranilate or dimethyl anthranilate. Methyl anthranilate is a non-lethal bird repellant. Anthranilate derivatives are generally non-toxic. Methyl anthranilate is also biodegradable affording no detectable residues and therefore poses little environmental threat. Although methyl anthranilate is non-toxic, it has been found that at relatively low concentrations it acts synergistically with metaldehyde to improve molluscicidal efficacy as well as targeting and so may greatly enhance the environmental profile of molluscicides.

In preferred embodiments of the invention, the repellant is d-pulegone. This repellant is a potent non-toxic bird repellant and is used as a harmless mint flavouring in human foods. The compound is a non-phytotoxic terpenoid and comes form the pennyroyal plant (*Mentha pulegium*). It is used at concentrations greater than 1% in food preparations. Concentrations as low as 0.01% have been shown to repel birds significantly and the compound has also been shown to repel dogs. D-Pulegone has been found to perform at least as well as anthranilate compounds in terms of molluscicide synergy and to be better at lower concentrations. It is 10 times as efficient a bird repellant as dimethyl anthranilate and comparatively inexpensive leading to cheaper molluscicide formulations.

The repellant may be present at a concentration of not more than 1%. Preferably the repellant is present at a concentration of not more than 0.5%. Such low concentrations of repellant have been found to satisfactorily avert avian and mammalian pests and results in a cheaper molluscicide.

Percentages and amounts used in this specification are by weight unless indicated otherwise.

The metaldehyde may be present at a concentration of not more than 6%. The metaldehyde may be present at a concentration of not more than 4%. The metaldehyde may be present at a concentration of not more than 2%.

According to a second aspect of the invention there is provided use of a molluscicide formulation consisting essentially of a non-toxic animal repellant and metaldehyde.

The animal repellant may be selected from: methyl anthranilate, isobutyl anthranilate, ethyl anthranilate, isobutyl methyl anthranilate, dimethyl anthranilate and d-pulegone.

The repellant may be present at a concentration of not more than 1%, preferably not more than 0.5%.

The metaldehyde may be present at a concentration of not more than 6%, preferably not more than 4%, or more preferably not more than 2%.

According to a third aspect of the invention there is provided a molluscicide formulation comprising 92–96.5% flour, 6–2% metaldehyde, 1–0.5% non-toxic animal repellant and 1% calcium propionate.

BRIEF DESCRIPTION OF THE DRAWINGS

The invention is further described by means of example, but not in any limiting sense, with reference to the accompanying drawings, of which.

Figure 1:
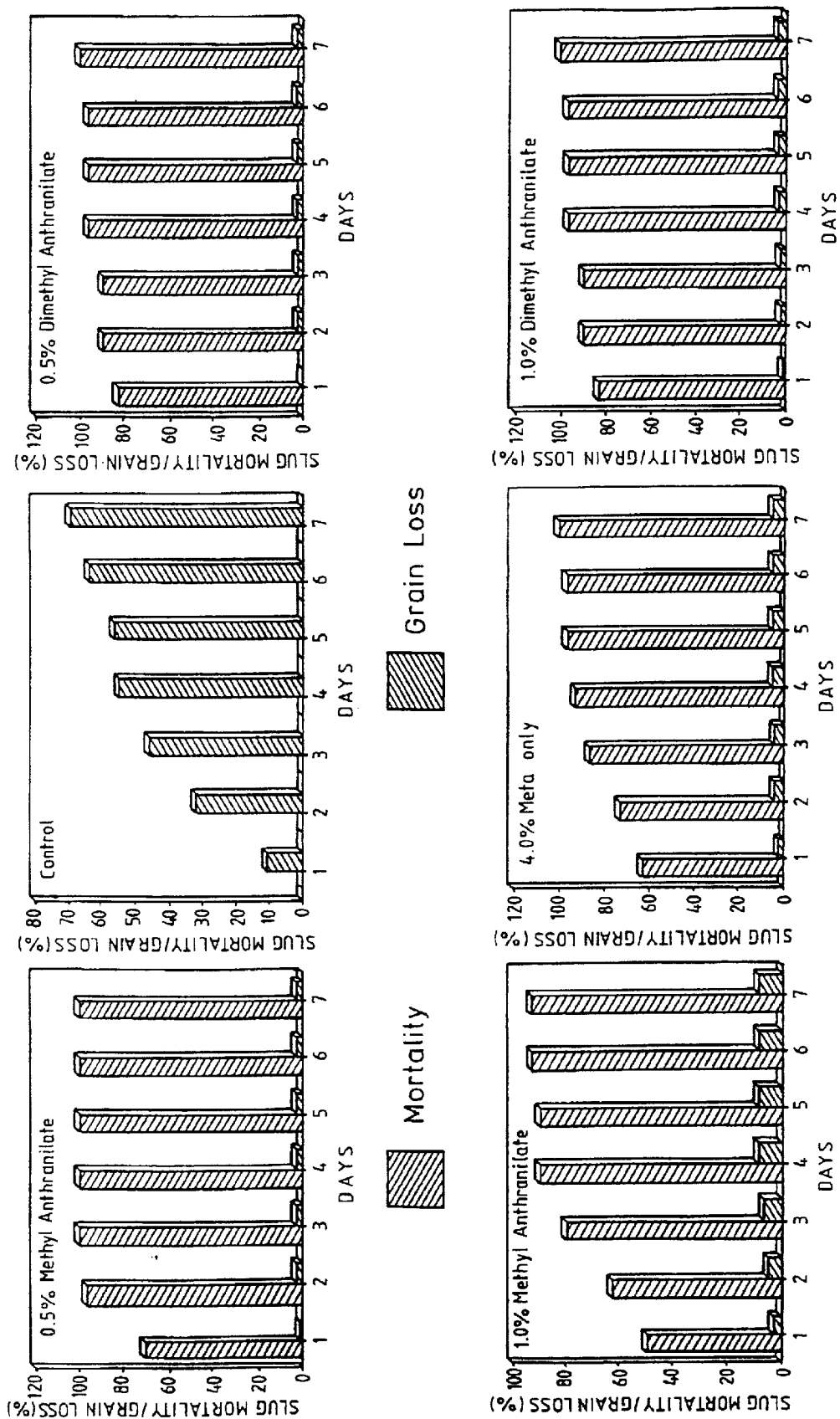
FIGS. 1–3 show a comparison of the mortality and grain loss rate in repellant and none repellant containing molluscicide formulations.

The synergistic advantage of combining a non-toxic bird and mammal repellant with a metaldehyde based molluscicide formulation has been demonstrated using a well established technique which simulates controlled field conditions.

Pellets were prepared by mixing Durum wheat flour with the following non-toxic repellents:

1. Methyl anthranilate (99.0% pure) BR1
2. Dimethyl anthranilate (95.0% pure) BR2
3. Methyl/Dimethyl Anthranilate (starch encapsulated at 19% w/w) BR3
4. D-Pulegone (95.0% pure) BR4 to give final concentrations of the repellents of 0.5% and 1%. Metaldehyde was added to the flour/repellant mixtures and thoroughly mixed to provide 2% and 4% metaldehyde w/w. The mixture was then compressed into small pellets having approximate dimensions of 5 mm by 2 mm. Similar pellets were made from metaldehyde and flour mixtures and flour only to provide control samples. The efficacy of the pellets was then tested in standardised terraria.

Test terraria in the form of trays measuring approximately 0.2 m2 had 100 wheat grains sown on a double thickness of filter paper as a test crop. Pellets were randomly added at the commercially recommended rate of approximately 200 g/100 m2. Five pre-starved slugs within a narrow weight band were introduced per terrarium tray and two trays per category per replicate were used. This rate represents a heavy slug infestation of 400,000 per hectare in the field. A total of three replicates were undertaken at 17° C. Using this technique the molluscicidal efficacy of 0.5% and 1% concentrations of the different repellents in a 4% metaldehyde molluscicide formulation was investigated by comparison with flour and metaldehyde pellets and flour pellets.

efficient at the lower concentration of 0.5%. The best performance was recorded for d-pulegone which achieved a 100% mortality rate at a concentration of 0.5% in 4% metaldehyde by the third day of exposure. D-Pulegone performed slightly better than methyl anthranilate (MA) when used at the 1% level. The repellents dimethyl anthranilate (DMA) and a starch encapsulated mixture of

TABLE 1

Mean data of three terraria trials showing slug mortality and grain loss.

| | | | | ALL FORMULATIONS CONTAIN 4.0% Metaldehyde | | | |
|---|---|---|---|---|---|---|---|
| | DAYS | CONTROL Blank | 4.0% Metaldehyde | 0.5% METHYL ANTHRANILATE X | 1.0% METHYL ANTHRANILATE | 0.5% DIMETHYL ANTHRANILATE | 1.0% DIMETHYL ANTHRANILATE |
| MORTALITY | 1 | — | 63.3 | 70.0 | 55.0 | 83.3 | 66.7 |
| % | 2 | — | 73.7 | 96.7 | 63.3 | 90.0 | 83.3 |
| | 3 | — | 86.7 | 100.0 | 80.0 | 90.0 | 90.0 |
| | 4 | — | 93.3 | 100.0 | 90.0 | 96.7 | 100.0 |
| | 5 | — | 96.7 | 100.0 | 90.0 | 96.7 | 100.0 |
| | 6 | — | 96.7 | 100.0 | 93.3 | 96.7 | 100.0 |
| | 7 | — | 100.0 | 100.0 | 93.3 | 100.0 | 100.0 |
| GRAIN | 1 | 10.7 | 2.3 | 0.7 | 2.7 | 1.0 | 1.7 |
| LOSS | 2 | 32.3 | 3.7 | 2.0 | 5.0 | 2.3 | 3.3 |
| (%) | 3 | 46.3 | 4.3 | 2.0 | 6.7 | 2.6 | 4.0 |
| | 4 | 55.0 | 5.0 | 2.0 | 8.7 | 3.0 | 4.3 |
| | 5 | 56.7 | 5.0 | 2.3 | 8.7 | 3.0 | 4.3 |
| | 6 | 64.0 | 5.0 | 2.3 | 8.7 | 3.3 | 4.3 |
| | 7 | 69.7 | 5.0 | 2.3 | 8.7 | 3.3 | 4.3 |
| NON-VIABLE GRAINS (%) | | 3.0 | 7.6 | 7.0 | 5.3 | 3.3 | 2.7 |
| MICROBIAL INFECTION (%) | | 1.0 | 1.0 | 0.3 | 0.7 | 1.3 | 0.7 |

| | | ALL FORMULATIONS CONTAIN 4.0% Metaldehyde | | | | | | |
|---|---|---|---|---|---|---|---|---|
| | DAYS | 0.5% METHYL/ DIMETHYL ANTHRANI-LATE | 1.0% METHYL/ DIMETHYL ANTHRANI-LATE | 0.5% D-PULEGONE X | 1.0% D-PULEGONE | 0.025% BI-TREX | 0.050% BI-TREX | 0.5% CINNAMA-MIDE | 1.0% CINNAMA-MIDE |
| MORTALITY | 1 | 66.7 | 53.3 | 63.3 | 70.0 | 53.3 | 60.0 | 63.2 | 50.0 |
| % | 2 | 90.0 | 76.7 | 96.7 | 90.0 | 80.0 | 80.0 | 80.0 | 66.7 |
| | 3 | 90.0 | 86.7 | 100.0 | 93.3 | 90.0 | 83.3 | 86.7 | 80.0 |
| | 4 | 100.0 | 90.0 | 100.0 | 93.3 | 90.0 | 90.0 | 86.7 | 83.3 |
| | 5 | 100.0 | 93.3 | 100.0 | 96.7 | 90.0 | 90.0 | 90.0 | 90.0 |
| | 6 | 100.0 | 96.7 | 100.0 | 96.7 | 93.3 | 90.0 | 93.3 | 90.0 |
| | 7 | 100.0 | 96.7 | 100.0 | 96.7 | 93.3 | 90.0 | 93.3 | 93.3 |
| GRAIN | 1 | 1.3 | 2.3 | 2.0 | 2.0 | 1.3 | 1.3 | 1.3 | 2.3 |
| LOSS | 2 | 3.3 | 9.7 | 2.3 | 3.3 | 5.0 | 4.3 | 3.7 | 8.0 |
| (%) | 3 | 4.0 | 12.3 | 2.3 | 4.0 | 6.3 | 4.6 | 6.0 | 9.3 |
| | 4 | 4.3 | 16.0 | 2.3 | 4.0 | 7.3 | 4.6 | 6.7 | 9.7 |
| | 5 | 4.3 | 17.0 | 2.3 | 4.0 | 9.0 | 4.6 | 7.0 | 9.7 |
| | 6 | 4.3 | 17.0 | 2.3 | 4.3 | 9.0 | 4.6 | 7.0 | 9.7 |
| | 7 | 4.3 | 17.0 | 2.3 | 4.3 | 9.3 | 5.0 | 7.0 | 10.3 |
| NON-VIABLE GRAINS (%) | | 4.3 | 0.7 | 2.7 | 3.0 | 0.3 | 2.3 | 5.7 | 5.7 |
| MICROBIAL INFECTION (%) | | 1.0 | 0.7 | — | 0.3 | 0.7 | — | 1.0 | 2.0 |

Figure 2:
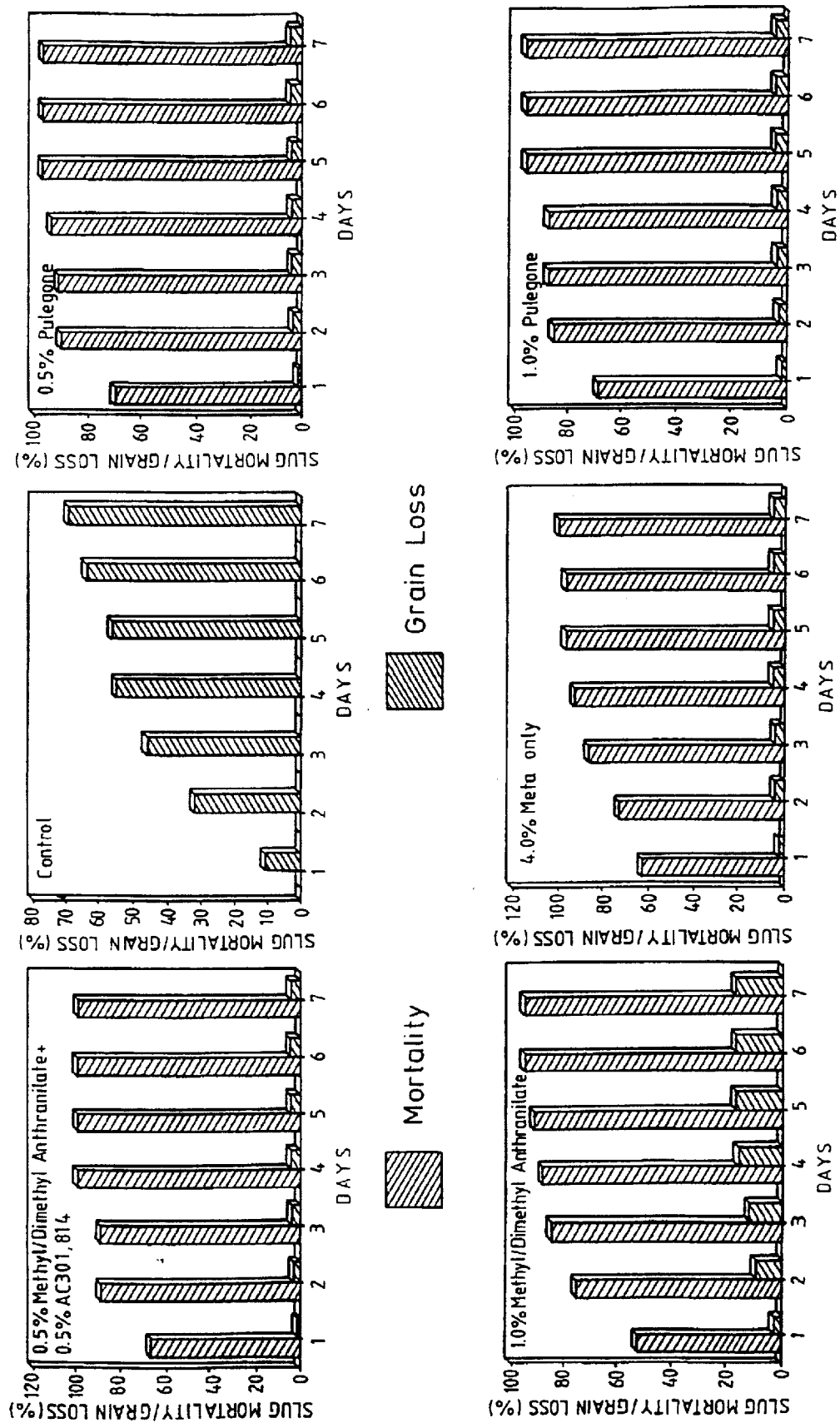
Figure 3:
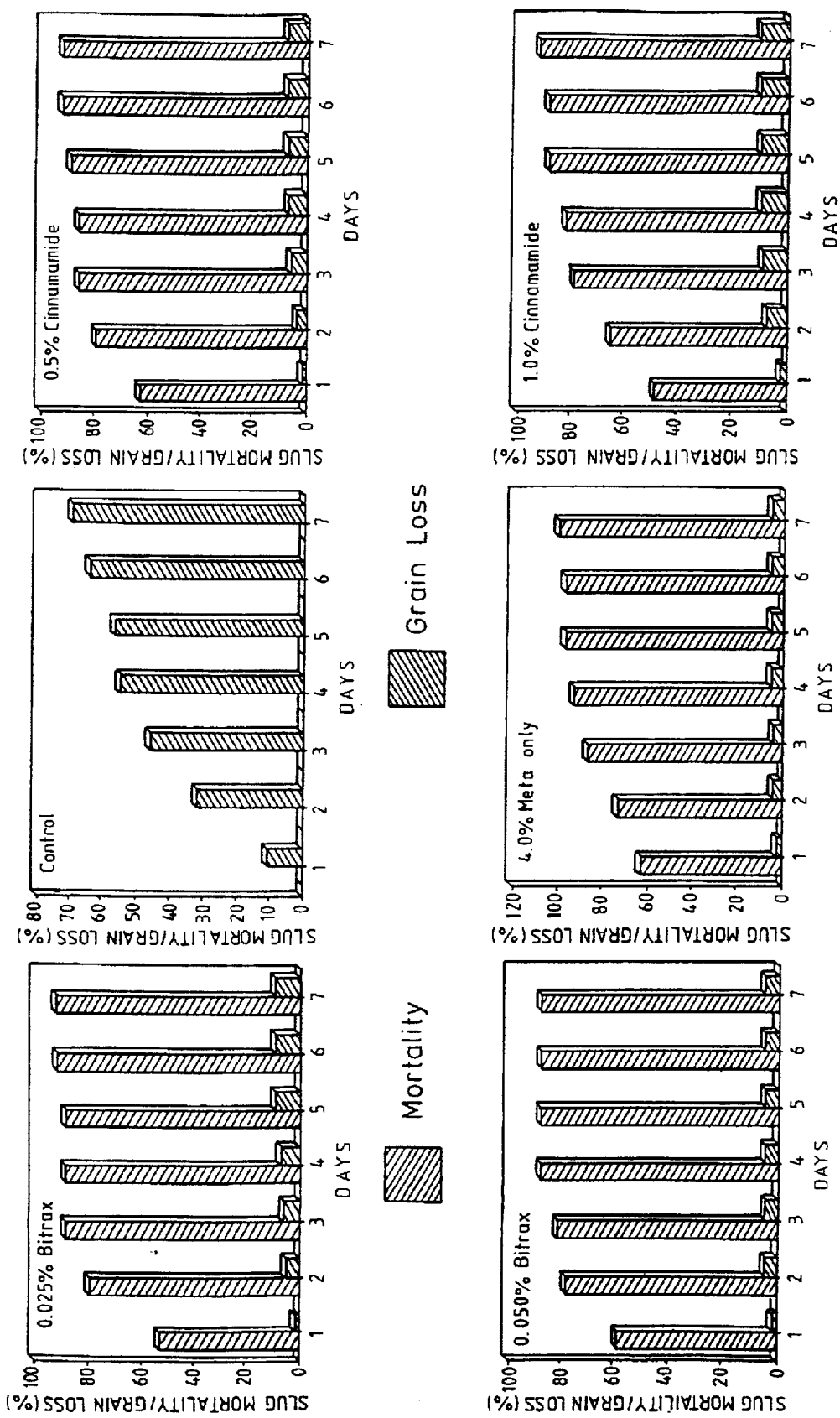

The results obtained using 4% metaldehyde as the molluscicide are summarized in Table 1. The mean data represent the results of three terraria trials and demonstrate % slug mortality and % grain loss obtained using different bird repellant additives. A certain amount of grain loss is recorded representing un-germinated or non-viable grains. The relative performance of bird repellents against each other and the control pellets is shown in FIGS. 1 to 3.

As can be seen the anthranilate and d-pulegone compounds enhance the molluscicidal efficacy at the concentrations added compared to the metaldehyde alone pellets. Methyl anthranilate is more efficacious at a concentration of 0.5% than at 1% and most of the repellents were more MA/DMA were found to closely follow D-pulegone and MA in terms of improved molluscicidal efficacy.

Figure 4A:
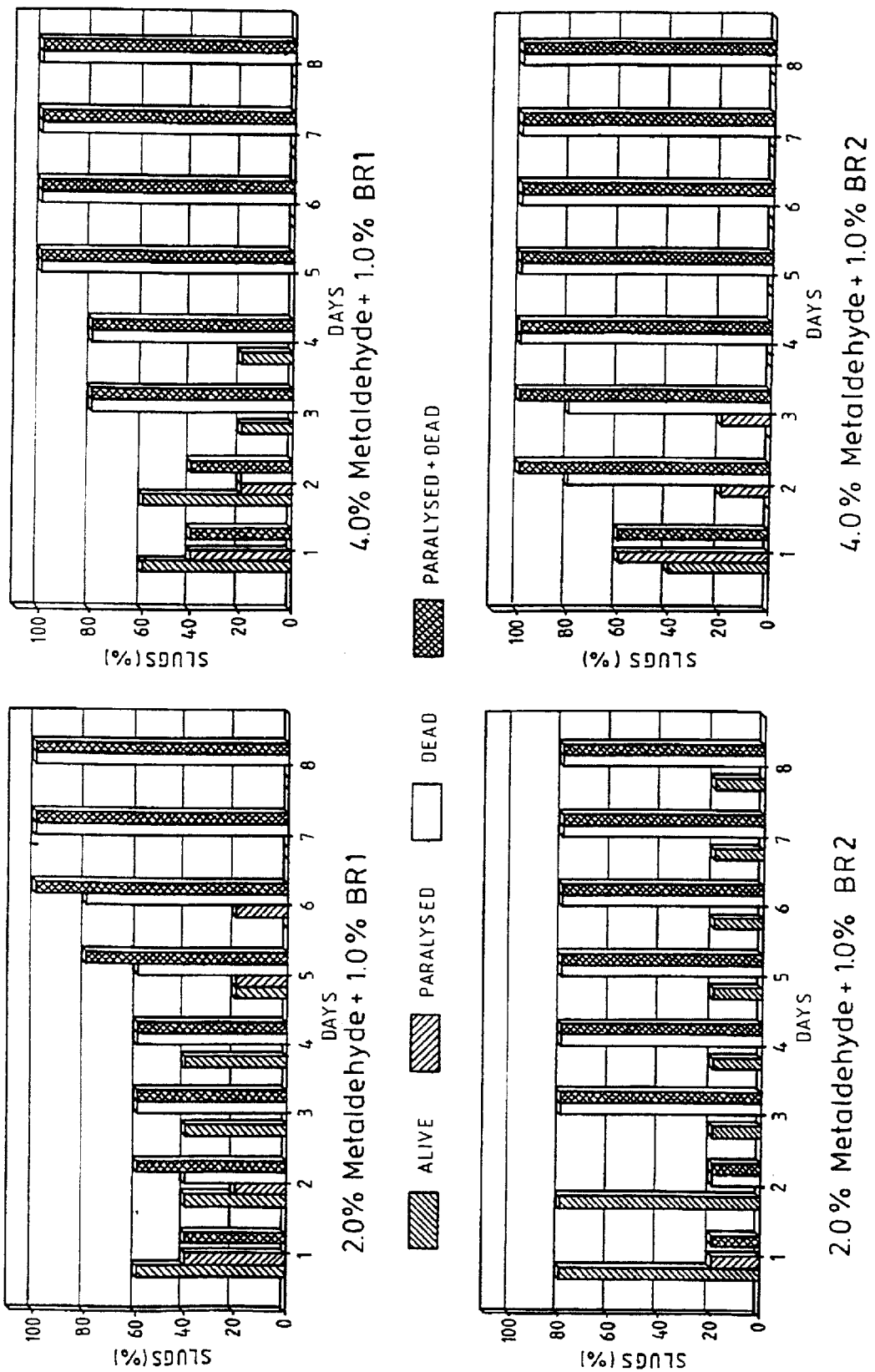
FIG. 4 shows a comparison of the efficacies of different amounts of metaldehyde in a repellant containing molluscicide formulation.
Figure 4B:
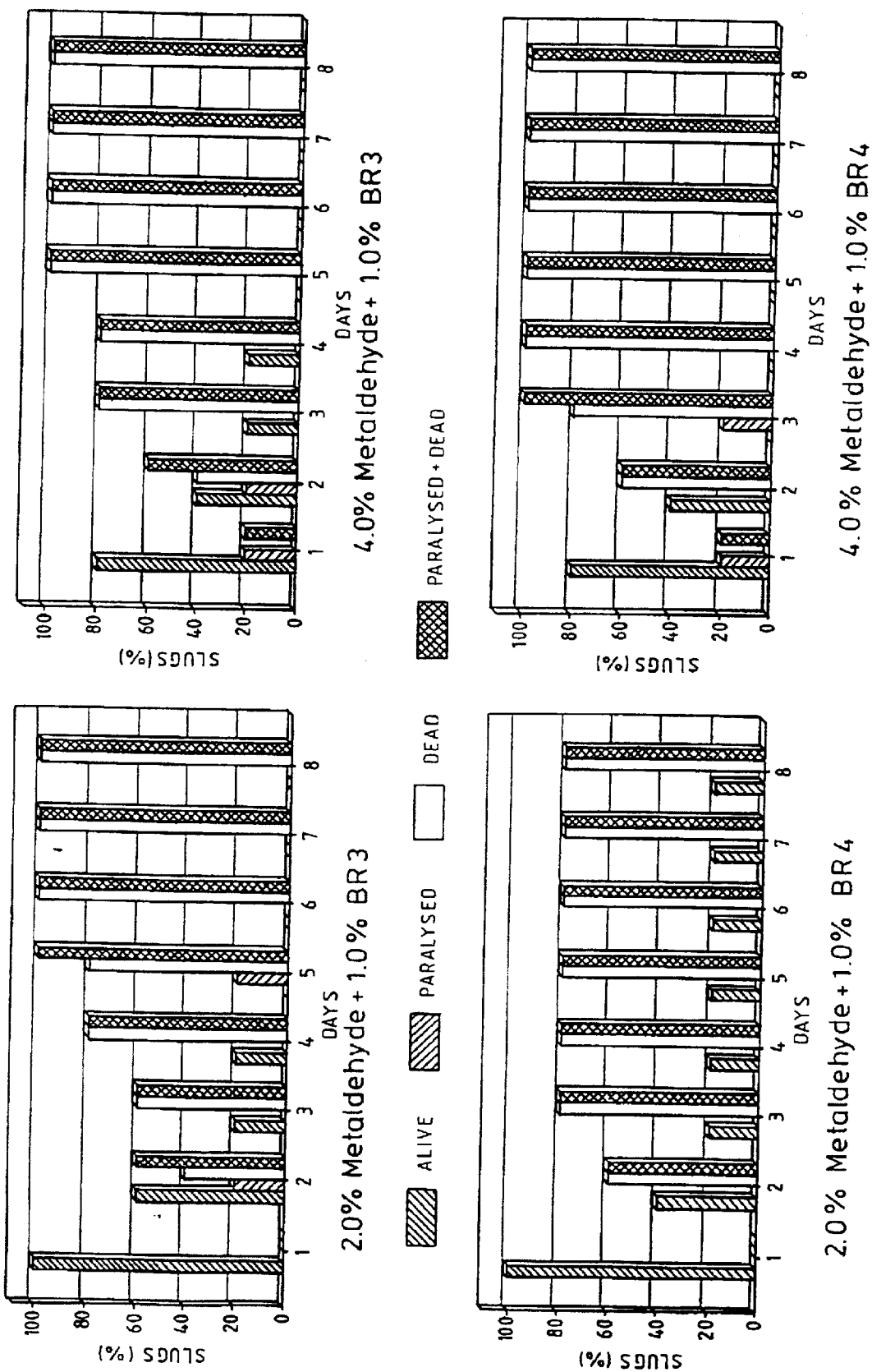

A comparison of the efficacy obtained at 2% metaldehyde and 4% metaldehyde using a 1% concentration of bird repellant additive was carried out using a similar experimental technique as before. FIG. 4 shows that overall 4% metaldehyde formulations are the most efficacious with d-pulegone and methyl anthranilate showing the greatest synergistic effect. Formulations containing 6% metaldehyde by weight are also envisaged.

Other animal repellant compounds such as bitrex and cinnamamide were not found to enhance the molluscicidal efficacy over that of the 4% metaldehyde alone formulation at the concentrations used.

What is claimed is:

1. A molluscicide formulation containing a non-toxic animal repellant and metaldehyde, wherein the repellant is an anthranilate compound or d-pulegone.

2. A formulation as claimed in claim 1, in which the animal repellant is a bird and/or mammal repellant.

3. A formulation as claimed in the claim 1, wherein the repellant is selected from the group consisting of: methyl anthranilate, isobutyl anthranilate, ethyl anthranilate, isobutyl N-methyl anthranilate and methyl N-methyl anthranilate.

4. A formulation as claimed in claim 1, in which the repellant is methyl anthranilate.

5. A formulation as claimed in claim 1, in which the repellant is methyl N-methyl anthranilate.

6. A formulation as claimed in claim 1, in which the repellant is present at a concentration of not more than 1 wt/wt %.

7. A formulation as claimed in claim 1, in which the repellant is present at a concentration of not more than 0.5 wt/wt %.

8. A formulation as claimed in claim 1, in which the metaldehyde is present at a concentration of not more than 6 wt/wt %.

9. A formulation as claimed in claim 1, in which the metaldehyde is present at a concentration of not more than 4 wt/wt %.

10. A formulation as claimed in claim 1, in which the metaldehyde is present at a concentration of not more than 2 wt/wt %.

11. A method of controlling molluscs comprising applying to a locus in need of mollusc control an effective amount of a molluscicide formulation comprising a non-toxic animal repellant and metaldehyde, in which the animal repellant is selected from the group consisting of: methyl anthranilate, isobutyl anthranilate, ethyl anthranilate, isobutyl N-methyl anthranilate, methyl N-methyl anthranilate and d-pulegone.

12. A method as claimed in claim 11, in which the repellant is present at a concentration of not more than 1 wt/wt %.

13. A method as claimed in claim 11, in which the repellant is present at a concentration of not more than 0.5 wt/wt %.

14. A method as claimed in claim 11, in which the metaldehyde is present at a concentration of not more than 6 wt/wt %.

15. A method as claimed in any of claim 11, in which the metaldehyde is present at a concentration of not more than 4 wt/wt %.

16. A method as claimed in any of claim 11, in which the metaldehyde is present at a concentration of not more than 2 wt/wt %.

17. A molluscicide formulation consisting of 92–96.5 wt/wt % flour, 2–6 wt/wt % metaldehyde, 1–0.5 wt/wt % non-toxic repellant and 1 wt/wt % calcium propionate.

* * * * *